United States Patent
Travis

(10) Patent No.: US 11,738,162 B1
(45) Date of Patent: Aug. 29, 2023

(54) INSERTABLE DEVICE TO PREVENT ASPIRATION OF STOMACH CONTENTS DURING VENTILATION AND INTUBATION

(71) Applicant: Nicholas Richard Travis, Seminole, FL (US)

(72) Inventor: Nicholas Richard Travis, Seminole, FL (US)

(*) Notice: Subject to any disclaimer, the term of this patent is extended or adjusted under 35 U.S.C. 154(b) by 693 days.

(21) Appl. No.: 16/654,328

(22) Filed: Oct. 16, 2019

Related U.S. Application Data

(63) Continuation-in-part of application No. 15/417,203, filed on Jan. 26, 2017, now Pat. No. 10,456,542.

(60) Provisional application No. 62/287,246, filed on Jan. 26, 2016.

(51) Int. Cl.
| | |
|---|---|
| *A61M 16/04* | (2006.01) |
| *A61M 25/10* | (2013.01) |
| *A61J 15/00* | (2006.01) |
| *A61M 25/00* | (2006.01) |

(52) U.S. Cl.
CPC ........ *A61M 16/0409* (2014.02); *A61J 15/0003* (2013.01); *A61J 15/0073* (2013.01); *A61J 15/0092* (2013.01); *A61J 15/0096* (2013.01); *A61M 25/0017* (2013.01); *A61M 25/10* (2013.01); *A61M 2210/1085* (2013.01)

(58) Field of Classification Search
CPC ...... A61M 25/1006; A61M 2025/1015; A61M 2025/1068; A61M 16/0409; A61J 15/0003; A61J 15/0073; A61J 15/0092
See application file for complete search history.

(56) References Cited

U.S. PATENT DOCUMENTS 9,028,442 B2* 5/2015 Solar et al. ........ A61M 25/1002
604/101.01

FOREIGN PATENT DOCUMENTS

EP 0321614 A1* 6/1989

* cited by examiner

*Primary Examiner* — Courtney B Fredrickson
(74) *Attorney, Agent, or Firm* — DANIEL S. POLLEY, P.A.

(57) ABSTRACT

A novel nasogastric tube, that when properly inserted within a person, blocks the esophagus of the person to prevent gastric contents from being aspirated. The tube can be left in place during direct langroscopy and the device can include a preferably inflatable balloon for obstructing the person's esophagus. This balloon can be preferably provided on a slidable tube that allows for head movement/flexion without movement of the balloon placement. The tube can be a dual or single lumen device. With a duel lumen device, a first lumen can be connected to a suction tubing to suction gastric contents from the distal end of the tube, while the other lumen can open up above the cuff to allow for easier ventilation with a bag valve mask/BVM. A novel endotracheal tube and novel indwelling catheter also incorporating a balloon component are also disclosed.

19 Claims, 17 Drawing Sheets

INSERTABLE DEVICE TO PREVENT ASPIRATION OF STOMACH CONTENTS DURING VENTILATION AND INTUBATION

This application is a continuation-in-part of U.S. Application Serial No. 15/417,203, filed Jan. 26, 2017, which claims priority to and the benefit of U.S. Application Serial No. 62/287,246, filed Jan. 26, 2016. Both of the above applications are incorporated by reference in their entireties for all purposes.

FIELD OF THE INVENTION

The invention relates generally to insertable medical devices and particularly to an insertable medical device for preventing or reducing aspiration of a person's stomach contents during a medical procedure.

BACKGROUND

Intubation or tracheal intubation refers to the process of placing a flexible plastic tube into a person's trachea in order maintain an open airway or to be used as a conduit through which to administer certain drugs to the person. Aspiration of stomach contents during or prior to intubation is a common issue, especially in the pre-hospital environment. The below described novel insertable medical device is directed to preventing or reducing aspiration during intubation, as well as other medical procedures.

SUMMARY OF THE DISCLOSURE

Disclosed is a novel nasogastric tube, that when properly inserted within a person, blocks the esophagus of the person to prevent gastric contents from being aspirated. The tube can be left in place during direct langroscopy and the device can include a preferably inflatable balloon for obstructing the person's esophagus. This balloon can be preferably on a slidable tube that allows for head movement/flexion without movement of the balloon placement. This helps to provide a constant seal during intubation attempts and helps to prevent tube dislodgment. The tube can be a dual or single lumen device. With a duel lumen device, a first lumen can be connected to a suction tubing to suction gastric contents from the distal end of the tube, while the other lumen can open up above the cuff to allow for easier ventilation with a bag valve mask/BVM. This lumen functions much like a nasal trumpet or nasopharyngeal airway/NPA.

The disclosed novel nasogastric tube provides protection against aspiration during direct laryngoscopic intubation. The disclosed tube also allows for intubation through the device and for direct visualization.

BRIEF DESCRIPTION OF THE DRAWINGS

FIG. 1A is a cross sectional view of a portion of the nasogastric tube medical device of FIG. 1 illustrating a non-limiting configuration or arrangement for the duel lumen in accordance with the present disclosure;

DETAILED DESCRIPTION

Figure 1:
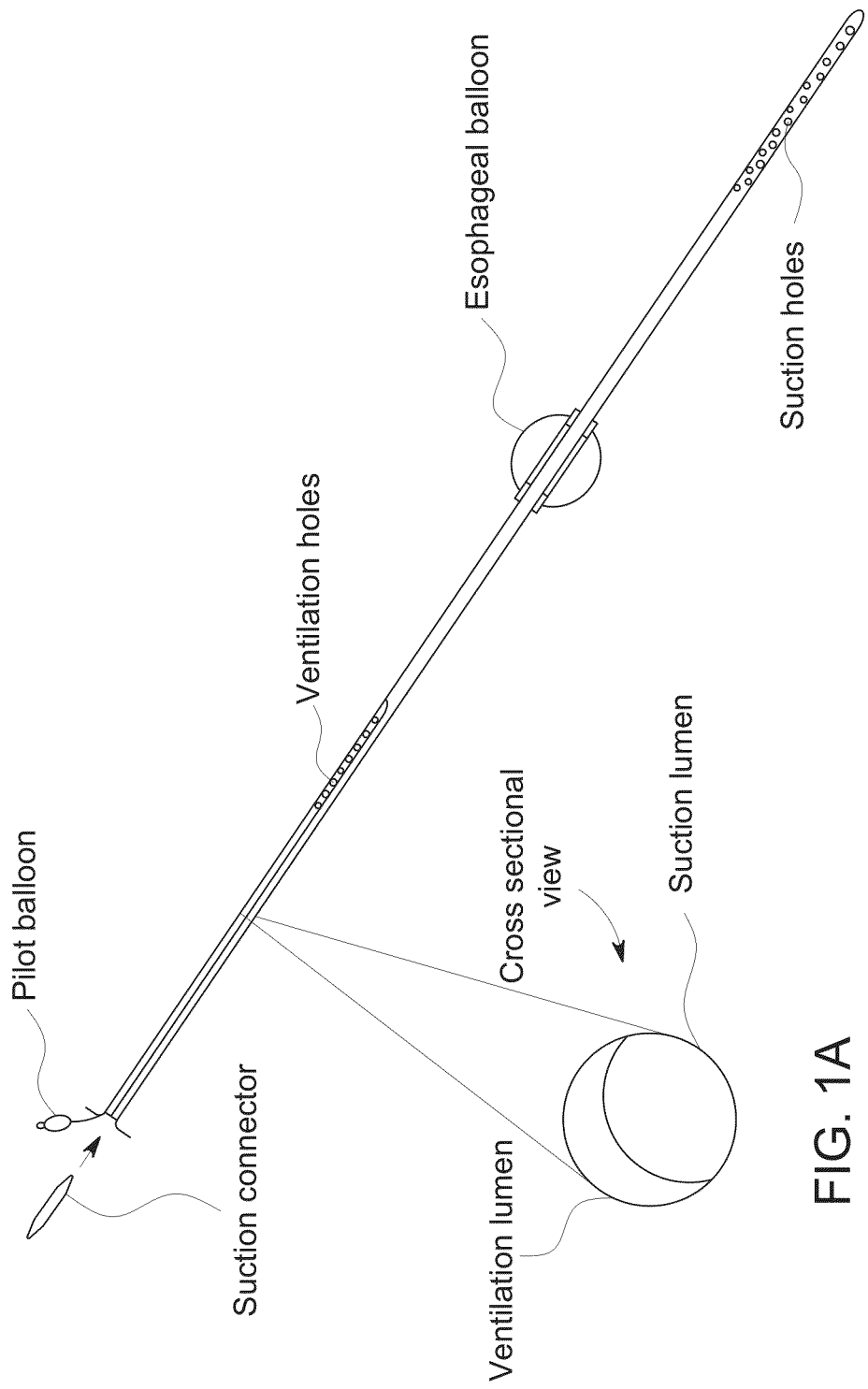
FIG. 1 is a perspective view of a novel nasogastric tube medical device, shown in a duel lumen embodiment in accordance with the present disclosure.

FIG. 1 shows a first embodiment for a novel nasogastric tube medical device in accordance with the present disclosure. As seen in FIG. 1, the tube has a first end which is preferably provided with one or more, and preferably a plurality of, suction holes. A dual lumen can be provided at the other end of the tube. One non-limiting configuration/arrangement for the dual lumen is shown in cross-sectional FIG. 1A, with one lumen preferably serving as a ventilation lumen and the other lumen preferably serving as a suction lumen. At least one, and preferably a plurality of, ventilation holes can be provided in a portion of the tube and provides communication between the ventilation lumen and the atmosphere outside of the disclosed nasogastric tube. Preferably, the ventilation lumen terminates at an intermediate length point of the tube, whereas the suction lumen can preferably extend the length of the tube. An esophageal balloon is preferably positioned externally along the tube at a point between the suction holes and the ventilation holes. A pilot balloon and a suction connector can be provided and/or secured at the end of the tube opposite of the suction holes. The preferred locations of the pilot balloon, ventilation holes, esophageal balloon and suction holes with respect to the elongated tube are illustrated. Also seen is a suction connector. As mentioned above, FIG. 1A shows a cross-sectional breakaway of the tube to better show one non-limiting configuration for the ventilation lumen and the suction lumen in the dual lumen embodiment. The ventilation lumen preferably provides an inner channel to bring air to the upper airway of the person/patient, to help deliver slightly more oxygen to the person/patient.

A relatively small tube connects or provides communication between a main blocking balloon and the pilot balloon. When installing the balloons are collapsed the second end of the inner tube (opposite end to the pilot balloon) is fed through the nostril and down the patient's/person's throat and into their esophagus. A flange/flared member at the first end is preferably larger in size than the person's/patient's nostril size thus causing the flange/flared member to act as a stop member. This stop member also preferably causes the main blocking balloon to be in proper position with the person's esophagus for its intended purpose. A portion of the inner tube can be previously cut based on measuring the inner tube length to a point on the person's chest, to help make sure the balloon and suction area are properly positioned. Once the device is properly positioned, a conventional syringe (air/nozzle) for inflating balloons can be used to inflate the main balloon. As the main balloon at this point is no longer visible (as it is inside the person's body - esophagus), the pilot balloon can be preferably provided so that the user knows how much the main balloon has been inflated. The pilot balloon is configured and set up to inflate at an equal or substantially equal amount to the main balloon to serve as a inflation guide or information source to the user. The second end of the inner tube can be closed or open and will work in either configuration.

Figure 2:
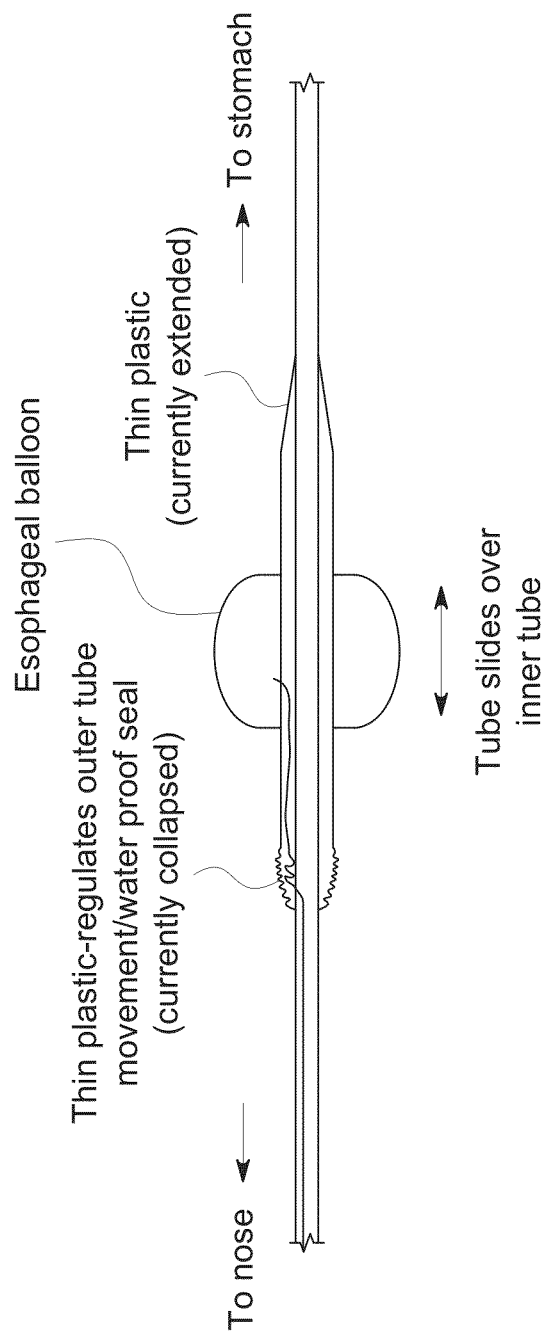
FIG. 2 is a front view of a portion of the nasogastric tube medical device of FIG. 1 illustrating a slidable portion and esophageal balloon.

FIG. 2 illustrates one non-limiting embodiment for a slidable portion/segment of the medical device and also shows the esophageal balloon, preferably secured to the outer tube. As seen, an outer tube is preferably positioned or slid over an inner tube and is slidable in its position with respect to the inner tube, which also changes the position of the esophageal balloon with respect to the inner tube. Thus, by preferably providing the balloon on a slidable tube, head movement/flexion by the person/patient is permitted without movement of the balloon placement inside the person. This helps to provide a constant seal during intubation attempts and helps to prevent tube dislodgment. A first relatively thin member (preferably thin plastic) can be provided. This member can regulate outer tube movement and provides for a waterproof seal (the member is shown collapsed) between the outer and inner tubes. A second relatively thin member (preferably thin plastic) can be provided at the opposite end of the outer tube and is shown in the figure in an extended position. The extended/collapsed positions of the thin members in FIG. 2 are considered non-limiting and the amount of extension/collapsing of each thin member can depend on the desired position of the outer tube with respect to the inner tube.

Figure 3:
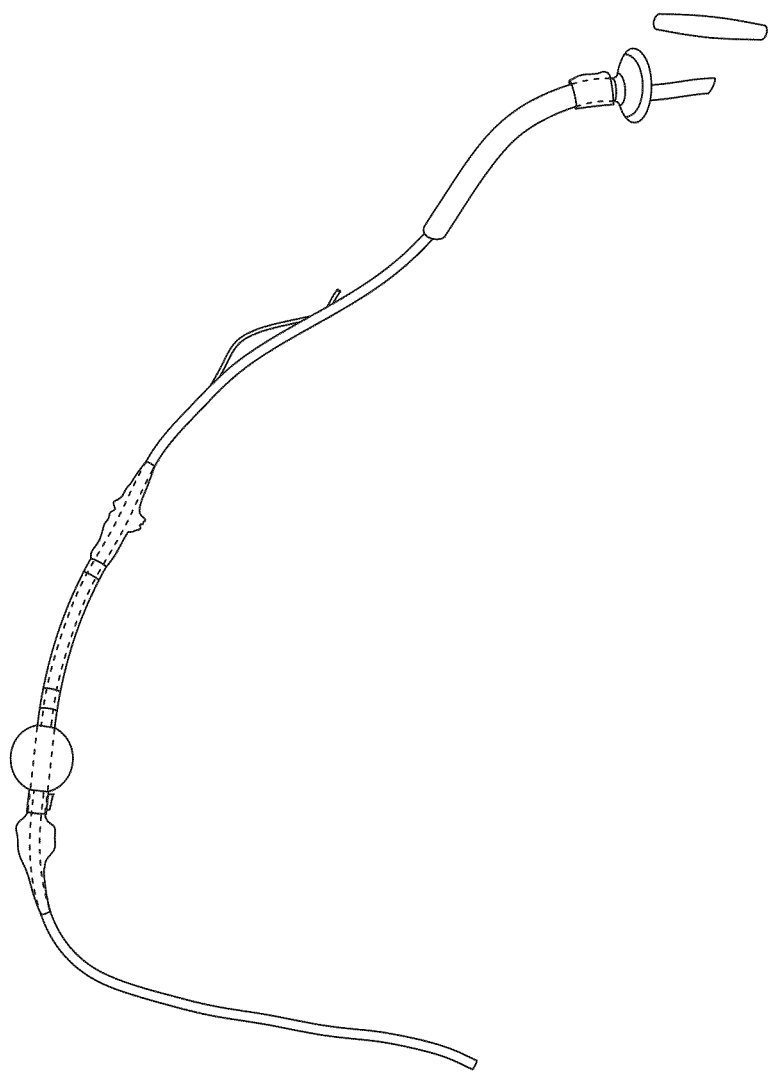
FIG. 3 is a perspective view of one embodiment for the nasogastric tube medical device in accordance with the present disclosure.
Figure 4:
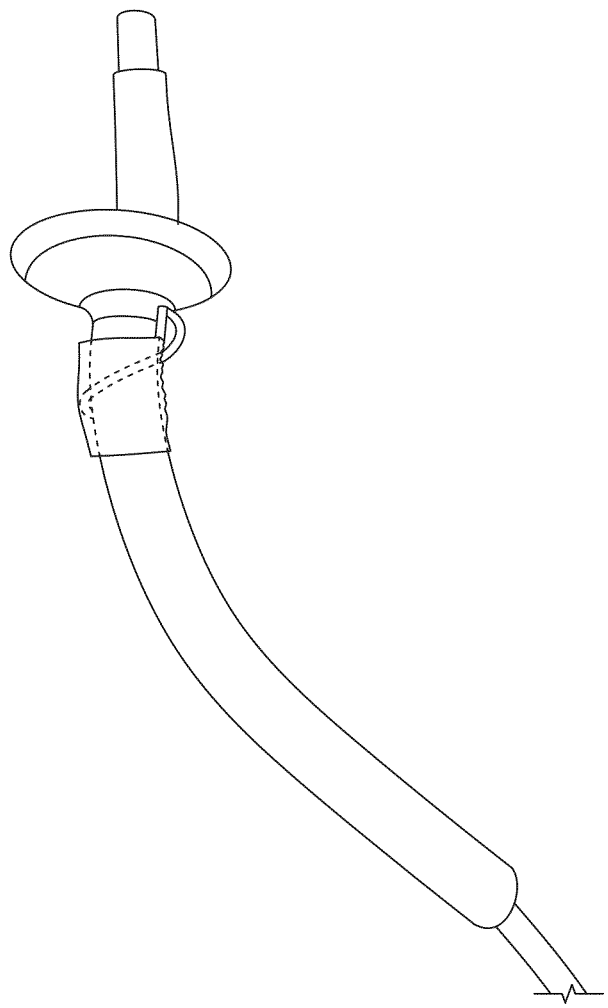
FIG. 4 is a close-up perspective view of a non-limiting nasal portion for the nasogastric tube medical device of FIG. 3.

FIG. 3 again shows the preferred novel nasogastric tube device. The top member, which is shown in green in the Figure, can be a nasal portion that preferably sits in the person's nose. The preferred flared or flanged outer end can sit flush with the nostril (See FIG. 7) and can serve as a stop member so that at least a relatively small portion of the medical device at the top end extends out of the person's/patient's nose. A pilot balloon can also stick out of the top of the medical device. A syringe can be attached to inflate the balloon, other inflating mechanisms can also be used and are considered within the scope of the disclosure. FIG. 4 shows a closer image of the nasal portion). Sitting separately can be the suction adaptor, which can attach to the nasal portion. The suction adaptor preferably attaches to the suction tubing. The ventilation holes on the elongated tube can be preferably located just below the end of the nasal portion (i.e. green segment in FIG. 4). At the bottom of the device/elongated tube multiple suction holes are preferably provided (See FIG. 3). The bottom portion can be cut or come in different sizes to compensate for different patient's/person's sizes who may need to use the disclosed medical device.

Various types of materials can be used for constructing the novel tube device, including, without limitation, rubber, polyvinyl chloride, polyethylene, silastic, latex, etc. and all are considered within the scope of the disclosure.

Figure 5:
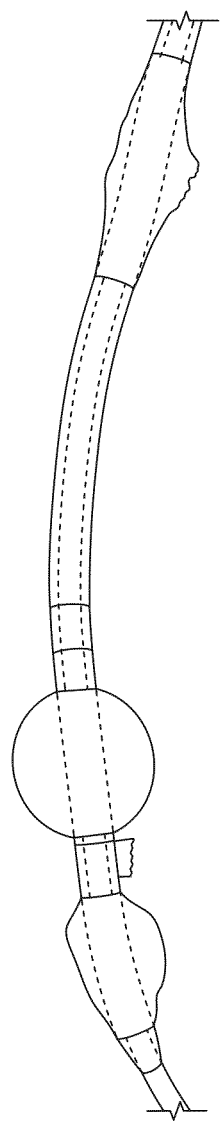
FIG. 5 is a close-up perspective view of a non-limiting sliding segment for the nasogastric tube medical device of FIG. 3.
Figure 6:
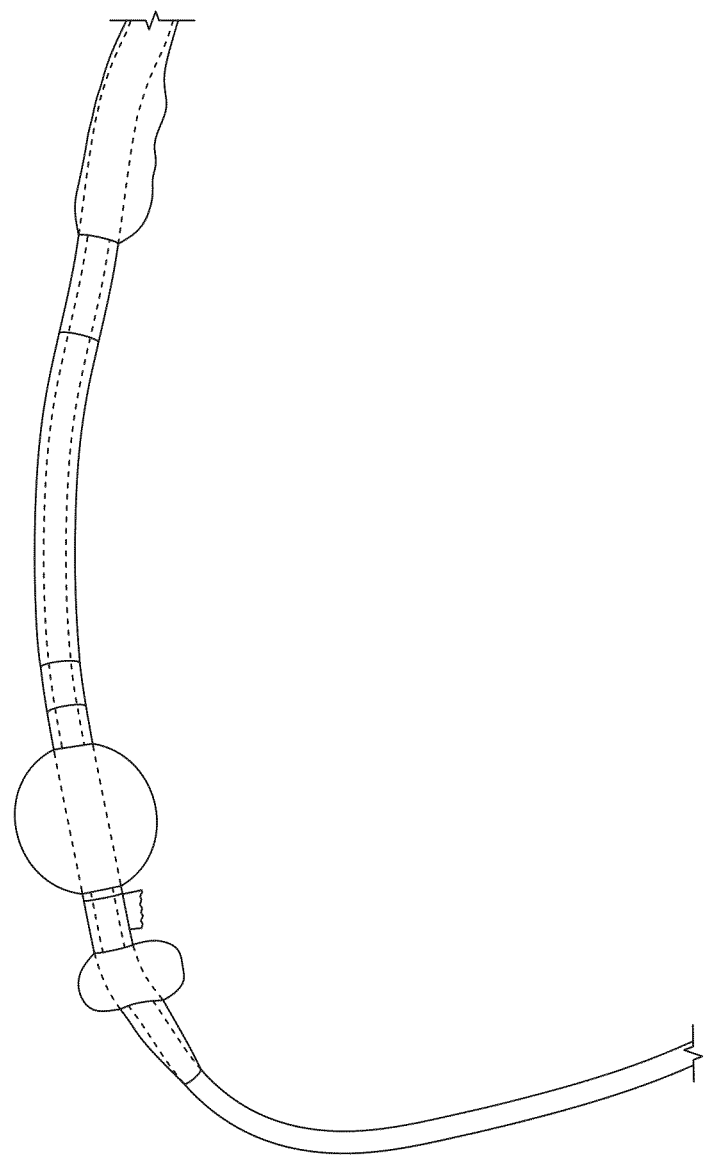
FIG. 6 is another closes-up perspective view of the non-limiting sliding segment for the nasogastric tube medical device of FIG. 3.
Figure 12:
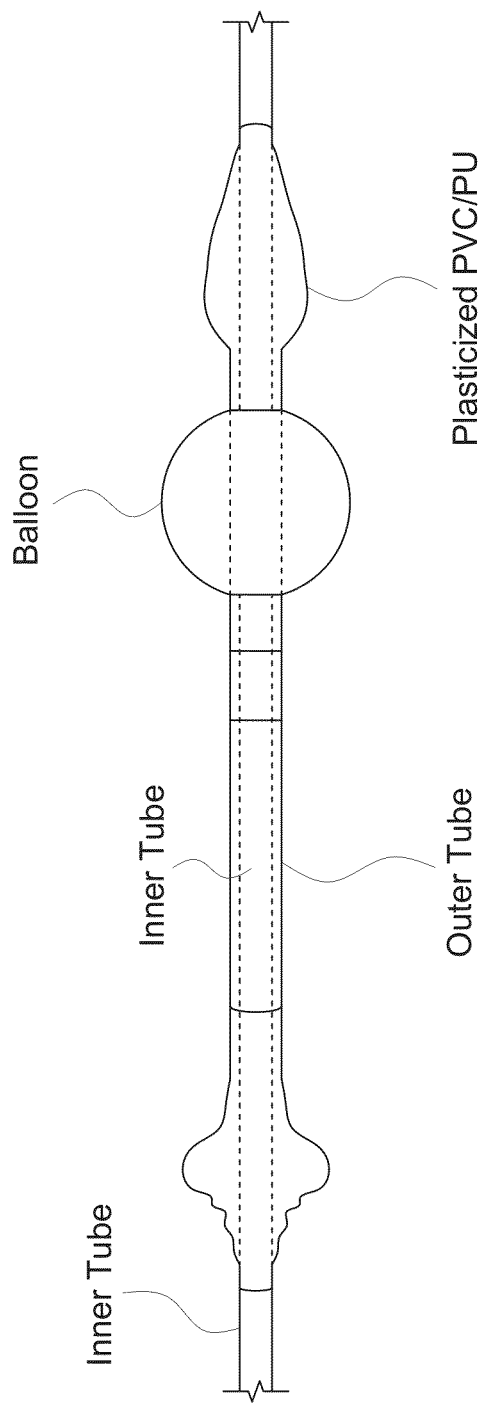
FIG. 12 is another close-up view of the sliding segment for the nasogastric tube medical device in accordance with the present disclosure and which can be used in both the single and duel lumen configurations.

FIGS. 5 and 6 show how the sliding segment works. The balloon itself can be made of a thin flexible plastic that is bonded or otherwise secured to the outer tube. All acceptable/medically safe securement techniques can be used for securing the balloon to the outer tube and all are considered within the scope of the disclosure. On each side/end of the outer tube, additional plastic members can be provided that are bonded (or otherwise secured) to both the inner and the outer tubes. These additional plastic members are preferably not inflated and are provided for also making the tubes waterproof and allows the outer tube to slide with respect to the inner tube. The plastic members restrict the distance that the outer tube can slide with respect to the inner tube (or vice versa). FIG. 12 is another close-up view of the sliding segment for the nasogastric tube medical device in accordance with the present disclosure and which can be used in both the single and duel lumen configurations. The outer tube preferably slides over the inner tube and then plasticized polyvinyl chloride (PVC)/polyurethane (PU) ("flexible or collapsible plastic") can be sealed/welded/adhered/otherwise secured on both the inner and outer tubes on each side of the outer tube. Besides creating a seal/fluid proof, the flexible or collapsible plastic prevent the outer tube from sliding too much in either direction along the inner tube. Thus, the sliding component of the disclosed medical device preferably comprises an outer tube that sits over the inner tube of the device. The obstructing balloon (i.e the balloon blocks the esophagus of the person to prevent gastric contents from being aspirated) can be preferably located on the slidable outer tube, thus, allowing for movement of the inner tube/outer tube positional relationship without the loss of movement/dislodgment of the obstructing balloon, especially where the person/patient moves his or her head. Movement of the outer tube can be regulated/restricted by the preferred plasticized PVC/PU end caps, which also waterproof/seal the slidable components/connections of the medical device.

Figure 7:
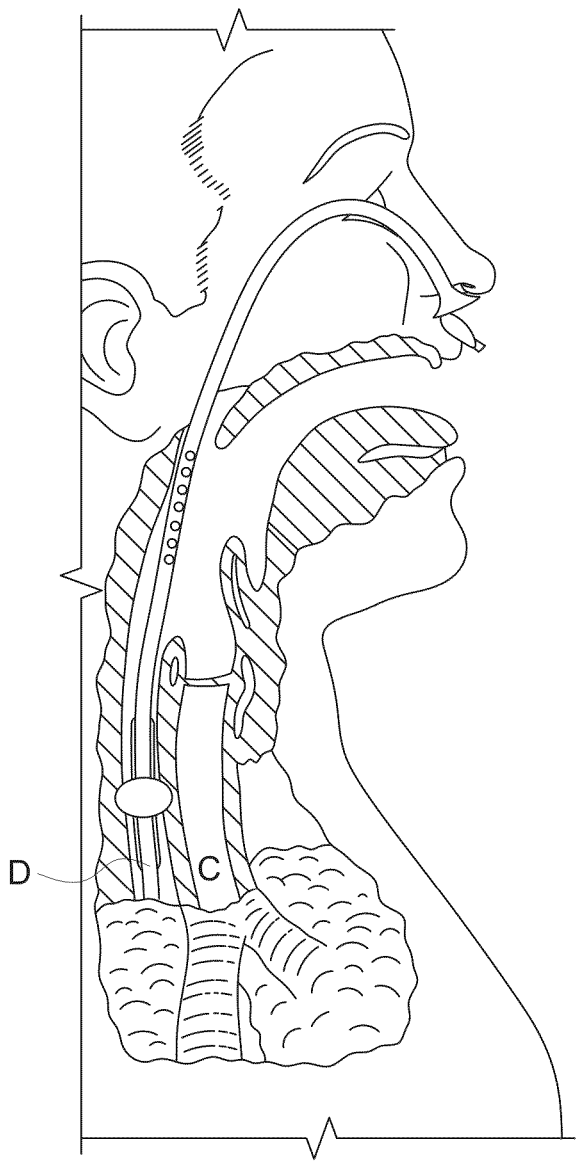
FIG. 7 illustrates how the nasogastric tube medical device sits in the airway of the person.
Figure 8:
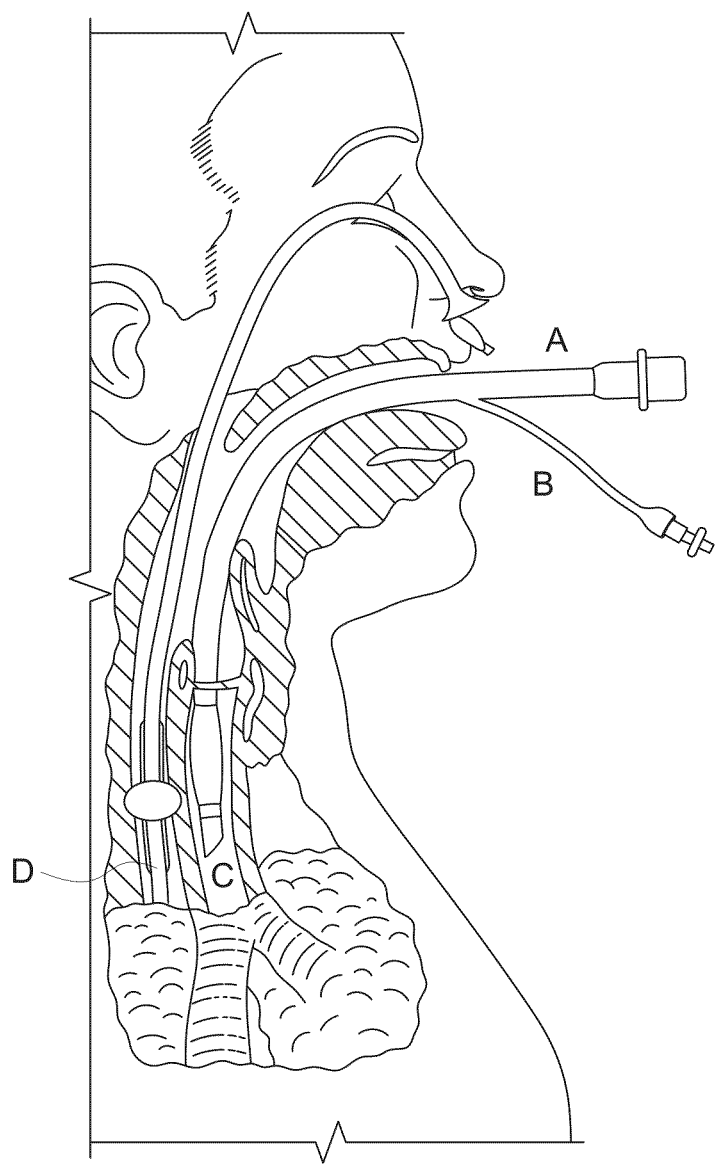
FIG. 8 also illustrates how the nasogastric tube medical device sits in the airway of the person and the medical device can be used in conjunction with an endotracheal tube/ ET tube.

FIGS. 7 and 8 show how the novel tube device (in green) will sit in the airway. Capital Letter "C" represents the person's/patient's trachea and capital letter "D" represents the person's/patient's esophagus. FIG. 8 also shows that device can be used in conjunction with an endotracheal tube/ ET tube. The distal portion of the device preferably sits in the person's stomach. When used with an ET tube, the novel tube device can be preferably inserted prior to the patient being intubated with the ET tube. The novel tube device shown and described herein prevent stomach contents from coming up the esophagus and going into the lungs while an ET tube is attempted to be placed for the person.

Figure 14:
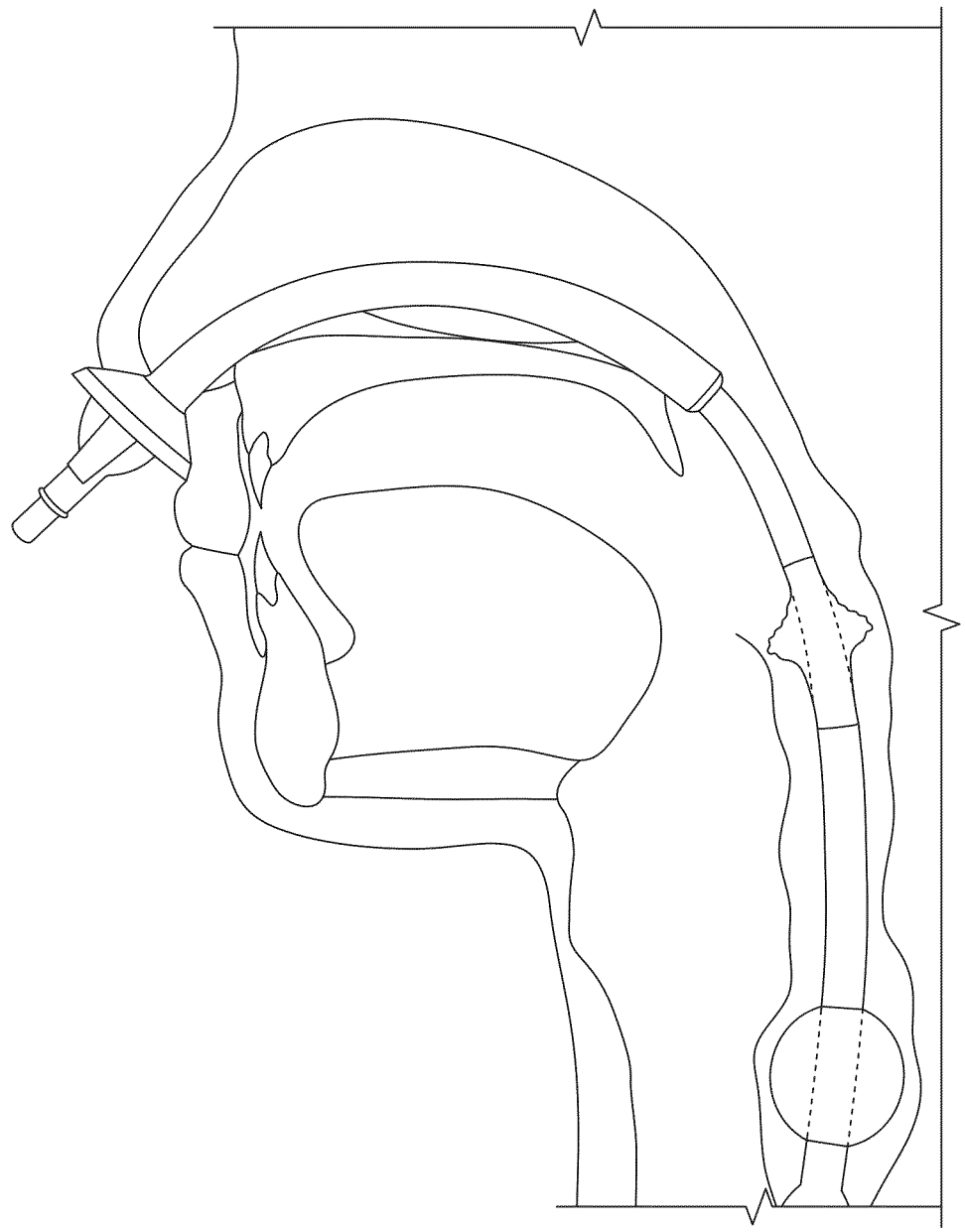
FIG. 14 is another view illustrating how the nasogastric tube medical device of the present disclosure sits in the airway of the person.

FIG. 14 provides a similar illustration showing how the nasogastric tube medical device in either configuration preferably sits in the airway of the person/patient.

Figure 9:
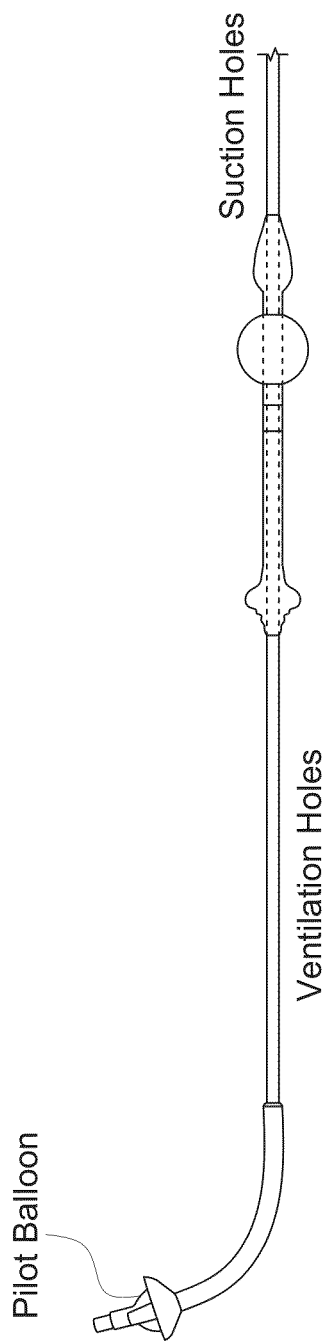
FIG. 9 is a front view of another embodiment for a duel lumen nasogastric tube medical device in accordance with the present disclosure and showing the device with both ventilation holes and with suction holes.
Figure 11:
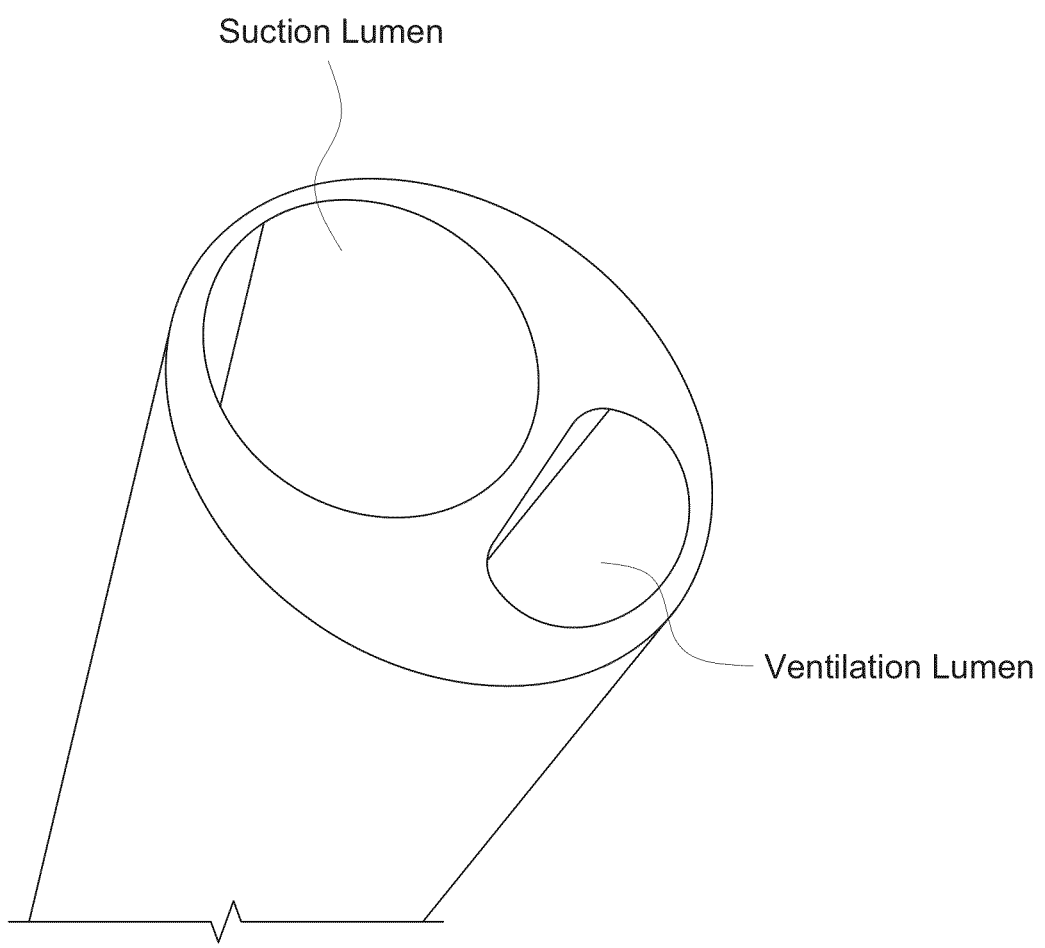
FIG. 11 is a close-up perspective view of the duel (suction and ventilation) lumen end for the nasogastric tube medical device of FIG. 9.

FIG. 9 illustrates another embodiment for a duel lumen nasogastric tube medical device in accordance with the present disclosure and showing the device with both ventilation holes and with suction holes. Like components described above are also applicable to the device shown in FIG. 9 and its operation and are incorporated by reference as if fully set forth herein. Along with a suction channel, the dual lumen preferably provides an inner channel (Ventilation Lumen) bringing air to the upper airway with the hope of delivering at least slightly more oxygen to the patient. FIG. 11 is a close-up of a non-limiting configuration of the duel (suction and ventilation) lumen end for the nasogastric tube medical device of FIG. 9

Figure 10:
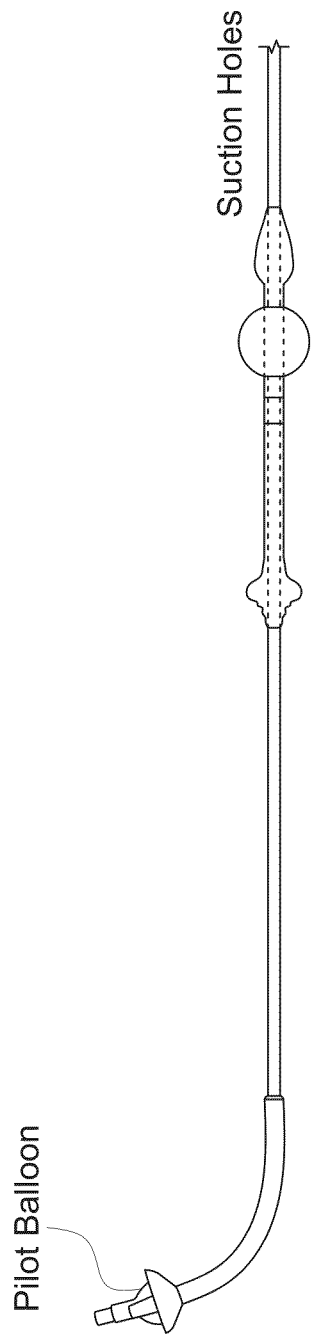
FIG. 10 is a front view of another embodiment for a single lumen nasogastric tube medical device in accordance with the present disclosure and showing the device with only suction holes.

FIG. 10 illustrates another embodiment for nasogastric tube medical device and which only uses a single lumen, that is preferably used for suction purposes. Thus, the device shown in FIG. 10 is only shown suction holes and without ventilation holes. Like components described above or shown in the drawings are also applicable to the device shown in FIG. 10 and its operation and are incorporated by reference. The single lumen preferably has only one channel, preferably the suction lumen. Thus, the single lumen design does not aid the person/patient in ventilation. However, it does allow for better suction capabilities for the removal of stomach contents.

Figure 13:
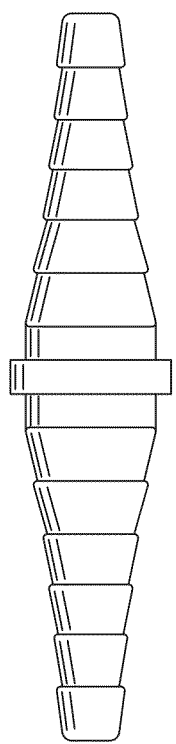
FIG. 13 is a perspective view of a non-limiting suction connector that can be used for connecting the nasogastric tube medical device to a suction device.

A non-limiting suction connector that can be used with the disclosed nasogastric tube medical device is shown in FIG. 13. The suction connector can be used for connecting the nasogastric tube medical device to a suction device. Preferably, the proximal end (top) of the device will include a suction connector with a removable cap. The suction connector allows the device to be connected to a suction device for the purpose of removing stomach contents and relieving gastric pressure.

Figure 15:
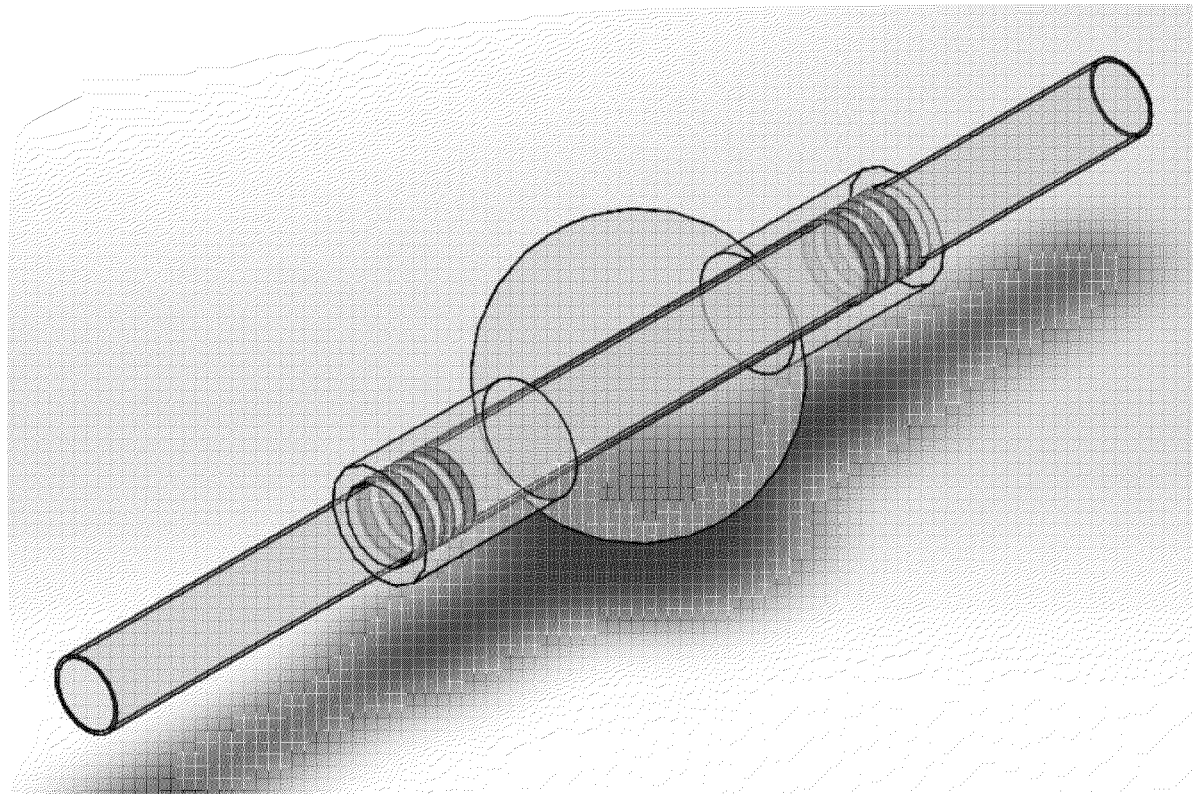
FIG. 15 illustrates an alternative embodiment for the balloon component for the nasogastric tube medical device in accordance with the present disclosure.

FIG. 15 illustrates an alternative embodiment for the balloon component for the disclosed novel device. In this non-limiting embodiment, one or more rods, constructed from TEFLON or similar material(s), can be placed/positioned between the outer and inner tubes to allow the balloon to slide while maintaining a watertight seal. Alternatively, the balloon may be attached directly to the rods. The rods can be used with or without the relatively thin plastic (See FIG. 2) member bonded or otherwise secured to the outer and inner tubes. However, when the plastic members are also still provided along with the rods, an improve watertight seal is provided and improved restriction of the tube movement is also achieved.

Figure 16:
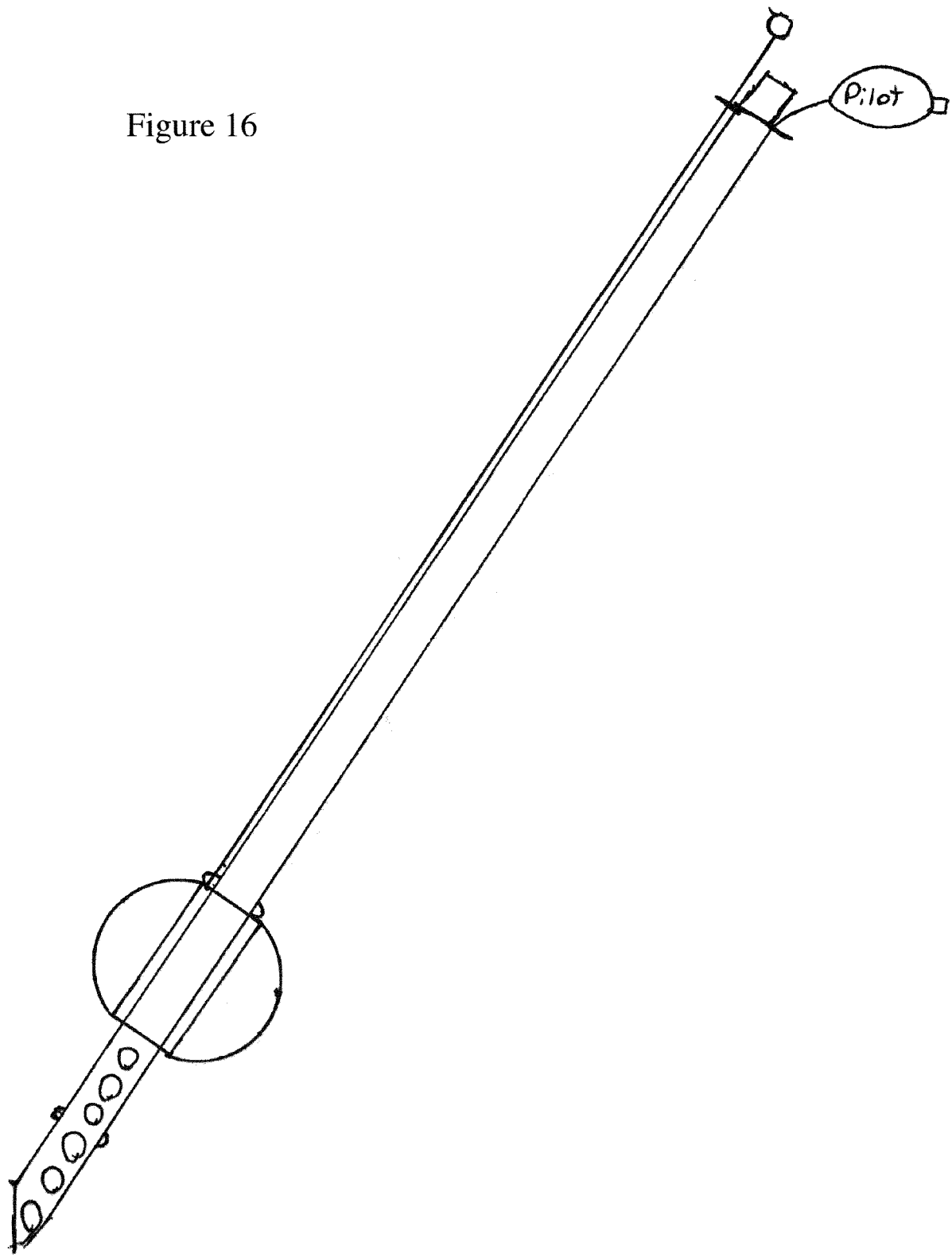
FIG. 16 illustrates a novel endotracheal tube having a slidable balloon component to prevent accidental and self-extubation in accordance with the present disclosure.

FIG. 16 illustrates a novel endotracheal tube having a slidable balloon component to prevent accidental and self-extubation. As seen, in a preferred embodiment, the endotracheal tube can be constructed and operate similar to a conventional endotracheal tube and can be silver coating and/or coated with another antimicrobial coating. A balloon component is preferably secured to a slidable outer section/tube similarly to the balloon component/outer tube described above and shown in the drawing in connection with the embodiments of FIGS. 1-15. The endotracheal tube can be with or without a suction lumen above cuff to clear laryngeal secretions. The distal end of the tube can be provided with at least one, and preferably a plurality (i.e. 2 or more) holes to provide adequate ventilation to the patient.

The novel device seen in FIG. 16 can be connected to an audible and/or visual alarm to indicate movement of the tube. The alarm can activate when the balloon segment slides a preset distance with respect to the inner tube, which can indicate the potential or possibility of tube dislodgment. The alarm may be built into the device itself or incorporated into a separate monitor which may be connected via electrical wire or wireless connection. Any conventional device for determining distance move can be used for determining when the balloon segment slid beyond the preset distance and all are considered within the scope of the disclosure.

Though not limiting, the novel device seen in FIG. 16 can be preferably provided with a small lumen, which can contain or house a cable that connects the slidable portion to a tab on the proximal end of the device. The tab can be pulled while advancing the tube to assist in tube readjustment and alarm reset. Alternatively, the cable may be combined with the pilot balloon lumen to perform the same function and the small lumen may not be needed. In this case, the pilot balloon tube can be reinforced (braid or otherwise) to prevent breakage of the tube.

Figure 17:
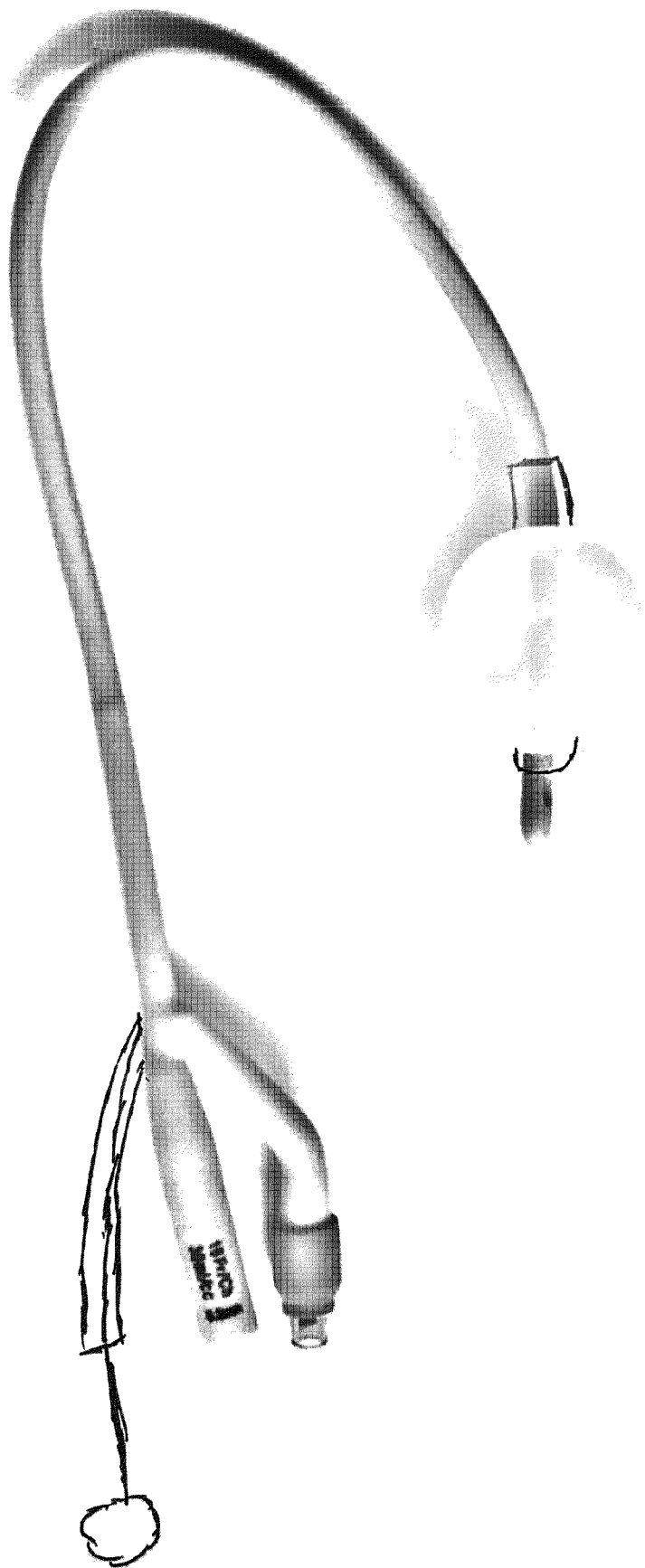
FIG. 17 illustrates a novel indwelling catheter having a slidable balloon to prevent traumatic removal in accordance with the present disclosure.

FIG. 17 illustrates a novel indwelling catheter having a slidable balloon to prevent traumatic removal. As seen, in a preferred embodiment, the indwelling catheter can be constructed and operate similar to a conventional indwelling catheter. The indwelling catheter can be provided with or without an antimicrobial coating. The novel indwelling catheter is shown preferably having a balloon component secured to a slidable outer section. The catheter can have a lumen for urine drainage with or without an additional lumen for bladder irrigation and/or medication administration. The distal end of the catheter may be standard or curved (coude) for use with difficult catheterizations.

The novel endotracheal tube and indwelling catheter described above can be provided with the movement restrictions (i.e. thin plastic, etc.) and sealing rods (i.e. TEFLON rods, etc.) described above.

The catheter can be connected to an audible and/or visual alarm to indicate movement of the catheter, which can be similar to the alarm discuss for the endotracheal tube. Thus, in a preferred embodiment, the alarm can activate when the balloon segment slides a preset distance, which can indicate the potential or possibility for catheter dislodgment. The alarm may be built into the device itself or incorporated into a separate monitor which may be connected via electrical wire or wireless connection.

A small additional lumen can be provided and contain a cable (including but not limited to plastic types) which connects the slidable portion to a tab on the proximal end of the device. The tab can be pulled while advancing the tube to assist in tube readjustment and alarm reset. Alternatively, the cable can be combined with the balloon inflation lumen to perform the same function. In this embodiment, the balloon lumen can be reinforced (braid or otherwise) to prevent breakage.

Like components described above or shown in the drawings for one device are also applicable to other devices shown and/or described in the application also containing the same or similar component and the descriptions are incorporated by reference for the other devices.

It should be understood that the exemplary embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from their spirit and scope.

All dimensions shown in the drawings are provided as non-limiting examples and other dimensions can be used and are considered within the scope of the disclosure All components of the described medical device and any part locations, dimensions, values, materials, attachment devices, positional relationships, etc. discussed above or shown in the drawings, if any, are merely by way of example and are not considered limiting and other part locations, dimensions, values, materials, attachment devices, positional relationships, etc. can be chosen and used and all are considered within the scope of the disclosure.

Unless feature(s), part(s), component(s), characteristic(s) or function(s) described in the specification or shown in the drawings for a claim element, claim step or claim term specifically appear in the claim with the claim element, claim step or claim term, then the inventor does not consider such feature(s), part(s), component(s), characteristic(s) or function(s) to be included for the claim element, claim step or claim term in the claim when and if the claim element, claim step or claim term is interpreted or construed. Similarly, with respect to any "means for" elements in the claims, the inventor considers such language to require only the minimal number of features, components, steps, or parts from the specification to achieve the function of the "means for" language and not all of the features, components, steps or parts describe in the specification that are related to the function of the "means for" language.

The benefits, advantages, solutions to problems, and any element(s) that may cause any benefit, advantage, or solution to occur or become more pronounced are not to be construed or considered as a critical, required, or essential features or elements of any or all the claims.

While the medical device has been described and disclosed in certain terms and has disclosed certain embodiments or modifications, persons skilled in the art who have acquainted themselves with this disclosure, will appreciate that it is not necessarily limited by such terms, nor to the specific embodiments and modification disclosed herein. Thus, a wide variety of alternatives, suggested by the teachings herein, can be practiced without departing from the spirit of the disclosure, and rights to such alternatives are particularly reserved and considered within the scope of the disclosure.

What is claimed is:

1. A nasogastric tube medical device for blocking the esophagus of a person to prevent gastric contents from being aspirated during a medical procedure, comprising:
   an elongated inner tube having a first end and a second end and a first length, the inner tube having at least one suction hole disposed near or at the second end of the inner tube, the inner tube having a first passageway extending from the first end to the second end; and
   a first balloon member secured to the inner tube;
   wherein the elongated inner tube having at least one ventilation hole disposed between a flange member and the at least one suction hole;
   wherein the first balloon member is slidably movable with respect to the elongated inner tube while also maintaining the first balloon member disposed between the at least one ventilation hole and the at least one suction hole in all movable positions for the first balloon member;
   wherein the elongated inner tube having a second passageway extending from the first end to an intermediate internal point prior to a position point of the first balloon member, the at least one ventilation hole provides communication between the second passageway and an atmosphere area external to the inner tube.

2. The medical device of claim 1 wherein the at least one ventilation hole is a plurality of ventilation holes disposed on a portion of the inner tube between the first balloon member and the flange member.

3. The medical device of claim 1 further comprising an outer tube having a first end and a second end and a second length and positioned on an outside portion of the inner tube between the at least one ventilation hole and the at least one suction hole, the first balloon member secured to the outer tube.

4. The medical device of claim 3 further comprising a first rod member disposed between the outer tube and the inner tube and a second rod member disposed between the outer tube and the inner tube.

5. The medical device of claim 4 further comprising a first collapsible/extendable member secured at the first end of the outer tube and to a first outside area of the inner tube and a second collapsible/extendable member secured at the second end of the outer tube and to a second outside area of the inner tube, the first collapsible/extendable member and the second collapsible/extendable member restricting an amount that the outer tube is permitted to move with respect to the inner tube in either direction.

6. The medical device of claim 3 wherein the outer tube is slidably secured to the outside portion of the inner tube.

7. The medical device of claim 6 further comprising a first collapsible/extendable member secured at the first end of the outer tube and to a first outside area of the inner tube and a second collapsible/extendable member secured at the second end of the outer tube and to a second outside area of the inner tube, the first collapsible/extendable member and the second collapsible/extendable member restricting an amount that the outer tube is permitted to move with respect to the inner tube in either direction.

8. The medical device of claim 3 further comprising a first means for sealing a first opening between the inner tube and the outer tube at or near the first end of the outer tube and a second means for sealing a second opening between the inner tube and the outer tube at or near the second end of the outer tube.

9. The medical device of claim 3 wherein the first balloon member is directly secured to the outer tube.

10. The medical device of claim 1 wherein the flange member is disposed at the first end of the inner tube.

11. The medical device of claim 1 wherein the elongated inner tube is flexible.

12. The medical device of claim 1 wherein the first balloon member is indirectly secured to the inner tube.

13. A nasogastric tube medical device for blocking the esophagus of a person to prevent gastric contents from being aspirated during a medical procedure, comprising:
   an elongated inner tube having a first end and a second end and a first length, the inner tube having at least one suction hole disposed near or at the second end of the inner tube, the inner tube having a first passageway extending from the first end to the second end; and
   a first balloon member secured to the inner tube;
   wherein the elongated inner tube having at least one ventilation hole disposed between the first end of the elongated inner tube and the at least one suction hole;
   wherein the first balloon member is positioned at all times between the at least one ventilation hole and the at least one suction hole;

wherein the elongated inner tube having a second passageway extending from the first end to an intermediate internal point prior to a position point of the first balloon member, the at least one ventilation hole provides communication between the second passageway and an atmosphere area external to the inner tube;

wherein the first balloon member is slidably movable with respect to the elongated inner tube while also maintaining the first balloon member disposed between the at least one ventilation hole and the at least one suction hole in all movable positions for the first balloon member.

14. The medical device of claim 13 further comprising a flange member disposed at the first end of the inner tube.

15. The medical device of claim 13 wherein the elongated inner tube is flexible.

16. A nasogastric tube medical device for blocking the esophagus of a person to prevent gastric contents from being aspirated during a medical procedure, comprising:
- an elongated inner tube having a first end and a second end and a first length, the inner tube having at least one suction hole disposed near or at the second end of the inner tube, the inner tube having a first passageway extending from the first end to the second end; and
- a first balloon member secured to the inner tube;
- wherein the elongated inner tube having at least one ventilation hole disposed between the first end of the elongated inner tube and the at least one suction hole;
- wherein the first balloon member is positioned at all times between the at least one ventilation hole and the at least one suction hole;
- wherein the elongated inner tube having a second passageway extending from the first end to an intermediate internal point prior to a position point of the first balloon member, the at least one ventilation hole provides communication between the second passageway and an atmosphere area external to the inner tube;
- further comprising an outer tube having a first end and a second end and a second length and positioned on an outside portion of the inner tube between the one or more ventilation holes and the one or more suction holes, the first balloon member secured to the outer tube; wherein the outer tube is slidably secured to the outside portion of the inner tube.

17. The medical device of claim 16 further comprising a first rod member disposed between the outer tube and the inner tube and a second rod member disposed between the outer tube and the inner tube.

18. The medical device of claim 13 further comprising a first collapsible/extendable member secured at the first end of the outer tube and to a first outside area of the inner tube and a second collapsible/extendable member secured at the second end of the outer tube and to a second outside area of the inner tube, the first collapsible/extendable member and the second collapsible/extendable member restricting an amount that the outer tube is permitted to move with respect to the inner tube in either direction.

19. The medical device of claim 16 further comprising a first means for sealing a first opening between the inner tube and the outer tube at or near the first end of the outer tube and a second means for sealing a second opening between the inner tube and the outer tube at or near the second end of the outer tube.

* * * * *